US00PP28768P2

(12) United States Plant Patent
Korlipara

(10) Patent No.: US PP28,768 P2
(45) Date of Patent: Dec. 12, 2017

(54) ***ECHINACEA* PLANT NAMED 'TNECHKR'**

(50) Latin Name: ***Echinacea* spp.**
Varietal Denomination: TNECHKR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,205

(22) Filed: Aug. 22, 2016

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct *Echinacea* plant named 'TNECHKR' characterized by an amazing number of very large inflorescences starting in the first season, very long bloom time with excellent rebloom, a very upright, compact habit, warm deep raspberry-colored ray florets surrounding dark cones, numerous, strong dark stems, and excellent vigor.

1 Drawing Sheet

Botanical denomination: *Echinacea* spp.
Variety designation: 'TNECHKR'.

BACKGROUND OF THE INVENTION

The present invention relates to a new and distinct cultivar of *Echinacea* and given the cultivar name 'TNECHKR'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Dixie Belle' (U.S. Plant Pat. No. 26,111), the new cultivar has more large inflorescences per plant with more ray florets per inflorescence, and ray florets that are deep raspberry rather than hot pink in color.

Compared to *Echinacea* 'Glowing Dream' (U.S. Plant Pat. No. 24,329), the new cultivar has larger inflorescences that are a deep raspberry color rather than deep coral pink.

This new *Echinacea* cultivar is uniquely distinguished by:

1. an amazing number of very large inflorescences starting in the first season,
2. very long bloom time with excellent rebloom,
3. very upright, compact habit,
4. deep raspberry-colored ray florets surrounding dark cones,
5. numerous, strong stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a group of *Echinacea* 'TNECHKR' as a two-year-old growing in the trial field in full sun in mid-July in Canby, Oreg.

FIG. 2 shows a single plant dug from this group in the garden.

DETAILED PLANT DESCRIPTION

The following is a detailed description of the new *Echinacea* cultivar based on observations of 2-year-old specimens growing in the trial field in July in full sun in Canby, Oreg. Canby is in Zone 8 on the USDA Hardiness map. Temperatures range from an average high of 95 degrees F. in August to an average of 32 degrees F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type.*—Herbaceous perennial.
*Hardiness.*—USDA Zones 4 to 9.
*Size.*—Grows to about 62 cm wide and 44 cm tall to top of inflorescences.
*Form.*—Basal clump, with about 22 stems from the base.
*Vigor.*—Excellent.
*Roots.*—Fibrous, with many downward growing and few laterals, ivory in color, Yellow White 158D, roots develop easily from cuttings from the crown.

Leaf (basal):

*Type.*—Simple.
*Shape.*—Lanceolate.
*Arrangement.*—Rosette.

*Blade size*.—Grows to 18 cm long and 0.5 cm wide.
*Margins*.—Serrate.
*Apex*.—Acuminate.
*Base*.—Attenuate.
*Surface texture*.—Strigose on both sides.
*Venation*.—Pinnate, Yellow Green 147C on both sides.
*Color*.—Topside Green N137A, bottom side closest to Yellow Green 147A.
*Petiole description*.—Clasping, grows to 19.5 cm long and 5 mm wide, scabrous, narrow leafy edges which fold upwards, topside Green 147A at top and blending to a base of Red Purple 39A, bottom side closest to Yellow Green 147B lightly tinted Red Purple 39B at base.

Leaf (stem):
*Type*.—Simple.
*Shape*.—Lanceolate.
*Arrangement*.—Alternate.
*Blade size*.—Grows to 12 cm long and 4 cm wide.
*Margins*.—Irregularly serrate.
*Apex*.—Acuminate.
*Base*.—Attenuate.
*Surface texture*.—Strigose on both sides.
*Venation*.—Pinnate, Yellow Green 147C on both sides.
*Color*.—Topside Green N137A, bottom side closest to Yellow Green 147A.
*Petiole description*.—Clasping, grows to 4.5 cm long and 5 mm wide, scabrous, narrow leafy edges, topside Green N137A on leafy edges and Yellow Green 147C in middle, bottom side closest to Yellow Green 147C.

Inflorescence:
*Type*.—Composite on terminal stalked heads.
*Number of flowering stems from the ground*.—About 22.
*Flowering stem*.—Grows to 36 cm tall from the base of the plant to the terminal inflorescence and can grow to 18 cm long from the top stem leaf to the base of an inflorescence; unbranched to branched, with 1 to 5 inflorescences per stem; diameter growing to 1 cm wide; strigose; Yellow Green 146B.
*Size*.—Grows to 11.5 cm wide and 4.5 cm deep as disc enlarges.
*Form*.—Ray florets held horizontally, mature disc is conic.
*Immature inflorescence* (*bud*).—2.5 cm wide and 2.3 mm deep, ray florets held upright at a 70 degree angle and rolled up so only the back color shows, Greyed Purple 187C except tip Yellow Green 145B, disc color Yellow Green 144A.
*Ray florets*.—Without pistil or stamen, about 25 in number, grow to 5 mm long and 13 mm wide, oblanceolate with the tip two-to-three-toothed (each acute), entire margins, base attenuate, glabrous on both sides; topside new closest to Red Purple 59A; bottom side Greyed Purple 186A; old florets topside Red Purple 61A, bottom side closest to Greyed Purple N186D.
*Disc*.—Flat becoming conic, becoming 4 cm deep and 4 cm wide with maturity, Greyed Purple 187A in background with bracts Red Orange 34B with tips Greyed Purple 187A.
*Disc florets*.—About 350 in number, each with 1 pistil and 4 stamen, grow to 10 mm long and 2.5 mm wide, each with one persistent, very stiff linear bract (12 mm long with the top 1 mm Greyed Purple 187A to 2 mm Red Purple 60A to 1 mm Yellow Orange 22A to 2 mm Yellow Green 144A blending to White NN155A on bottom); corolla 6 mm long and 2 mm wide, tubular, 5 lobed, glabrous and glossy, Greyed Purple N186C to N186D; pistil 10 mm long, ovary 3.5 mm long, White NN155D with top Yellow Green 145B, style 6 mm long Greyed Red 181D on bottom half and Greyed Purple 187A on top half, 2-branched stigma spreading 3.5 mm wide, Greyed Purple 187A; stamen 5 mm long, filaments 2 mm long and White NN155B, anthers 3 mm long and Greyed Brown N199A, pollen Yellow Orange 20A.
*Involucral bracts*.—In 4 leafy series, area grows to 38 mm wide and 15 mm deep, lobes lanceolate in shape, reflexed, grow to 12 mm long and 3 mm wide, Green N137A, margins strigose, tip acute, strigose on both sides.
*Receptacle*.—Grows to 15 mm wide and 25 mm deep, White NN155B.
*Bloom period*.—June through October in Canby, Oreg.
*Fragrance*.—Floral, sweet, light.
*Lastingness*.—Each inflorescence lasts about two weeks in Canby, Oreg.

Seeds: 3 mm long and 2.5 mm wide, oval, Brown 200C.
*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

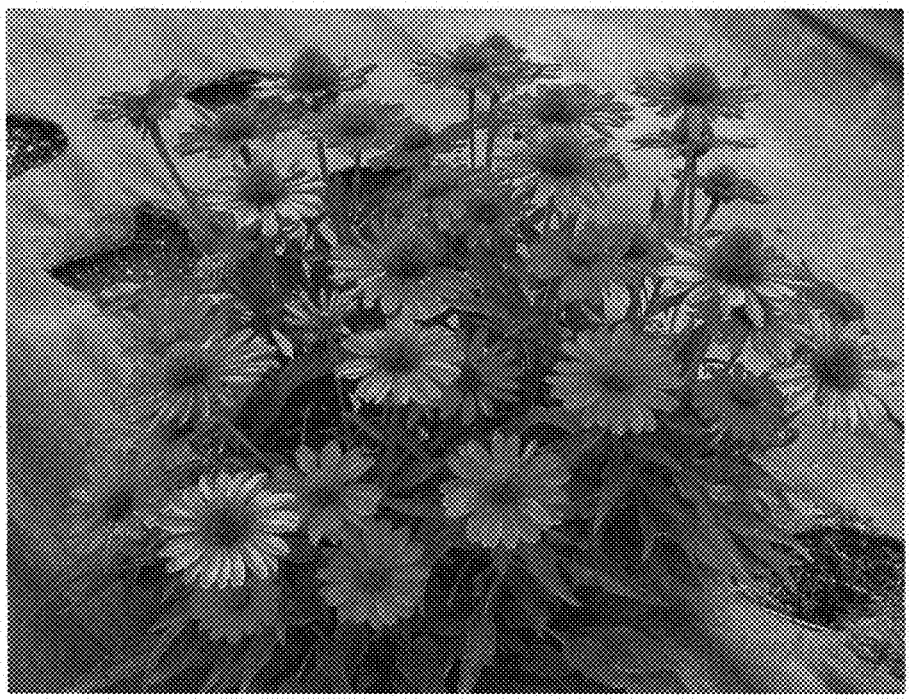

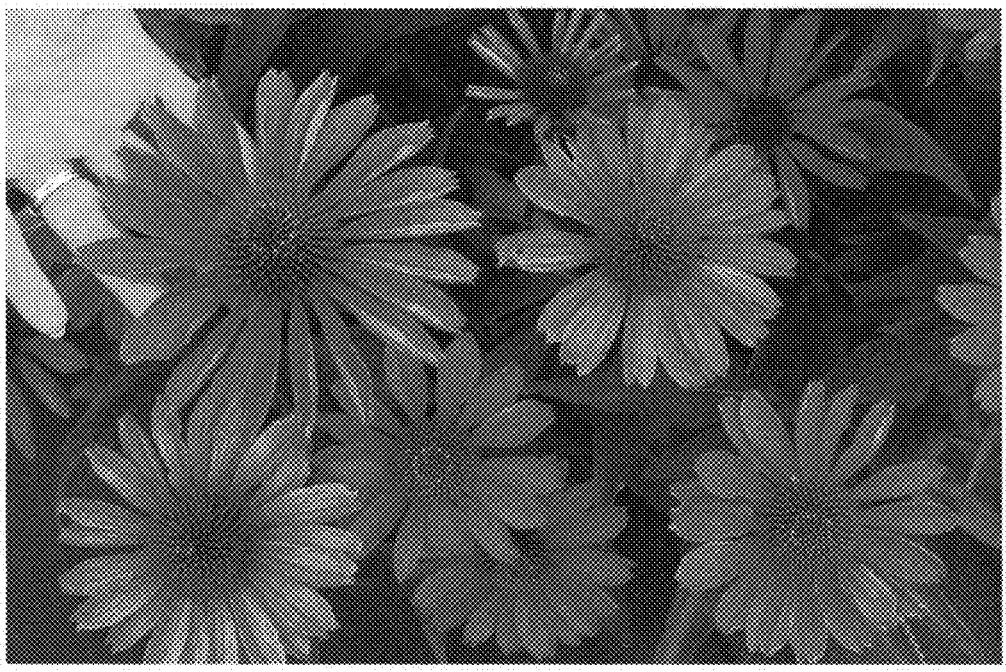
FIG. 1 above, FIG. 2 below